US008192719B2

(12) United States Patent
Larsen

(10) Patent No.: US 8,192,719 B2
(45) Date of Patent: Jun. 5, 2012

(54) METHODS AND KITS TO DIAGNOSE GROWTH HORMONE DEFICIENCY BY ORAL ADMINISTRATION OF EP 1572 OR EP 1573 COMPOUNDS

(75) Inventor: Finn Larsen, Edinburgh (GB)

(73) Assignee: Aeterna Zentaris GmbH, Frankfurt (DE)

( * ) Notice: Subject to any disclaimer, the term of this patent is extended or adjusted under 35 U.S.C. 154(b) by 235 days.

(21) Appl. No.: 12/279,805

(22) PCT Filed: Feb. 19, 2007

(86) PCT No.: PCT/GB2007/000566
§ 371 (c)(1),
(2), (4) Date: Jun. 8, 2009

(87) PCT Pub. No.: WO2007/093820
PCT Pub. Date: Aug. 23, 2007

(65) Prior Publication Data
US 2009/0305300 A1 Dec. 10, 2009

(30) Foreign Application Priority Data

Feb. 18, 2006 (GB) .................................. 0603295.7

(51) Int. Cl.
A61K 49/10 (2006.01)
G01N 33/74 (2006.01)
G01N 33/50 (2006.01)
A61K 38/27 (2006.01)
(52) U.S. Cl. ............... 424/9.2; 514/5.1; 514/113; 702/9
(58) Field of Classification Search .................. None
See application file for complete search history.

(56) References Cited

U.S. PATENT DOCUMENTS

| 4,853,371 | A | 8/1989 | Coy et al. |
| 5,635,379 | A | 6/1997 | Deghenghi |
| 5,646,301 | A | 7/1997 | Deghenghi |
| 5,668,254 | A | 9/1997 | Deghenghi |
| 5,798,337 | A | 8/1998 | Somers et al. |
| 5,811,074 | A | 9/1998 | Bercu et al. |
| 5,872,100 | A | 2/1999 | Deghenghi |
| 5,955,421 | A | 9/1999 | Deghenghi |
| 6,025,471 | A | 2/2000 | Deghenghi |
| 6,468,974 | B1 | 10/2002 | Bowers et al. |
| 6,730,498 | B1 | 5/2004 | Goodwin et al. |

FOREIGN PATENT DOCUMENTS

| WO | 91/18016 A1 | 11/1991 |
| WO | 94/11396 A1 | 5/1994 |
| WO | 94/11397 A1 | 5/1994 |
| WO | 95/14666 A1 | 6/1995 |
| WO | 96/10040 A1 | 4/1996 |
| WO | 96/15148 A2 | 5/1996 |
| WO | 96/29002 A | 9/1996 |
| WO | 97/22620 A1 | 6/1997 |
| WO | 99/39730 A1 | 8/1999 |
| WO | 99/62539 A1 | 12/1999 |
| WO | 01/96300 A | 12/2001 |

OTHER PUBLICATIONS

Beglinger et al., "Growth Hormone (GH) Stimulating Effects of a New, Orally Active Growth Hormone Secretagogue (EP 01572) in Healthy Males Following Oral and Intra-Duodenal Administration," The Endocrine Society's 88th Annual Meeting (2006).
Biller et al., "Sensitivity and Specificity of Six Tests for the Diagnosis of Adult GH Deficiency," J. Clin. Endocrinol. Metab. 87(5):2067-2079 (2002).
Bowers, C.Y., "GH Releasing Peptides-Structure and Kinetics," J. of Ped. Endocrinol. 6(1):21-31 (1993).
Bowers, Cyril Y., "Xenobiotic Growth Hormone Secretagogues: Growth Hormone Releasing Peptides," in Growth Hormone Secretagogues pp. 9-28 (Barry B. Bercu and Richard F. Walker eds., Springer-Verlay New York, Inc. 1996).
Casanueva et al., "Growth Hormone Secretagogues: Physiological Role and Clinical Utility," TEM 10(1):30-38 (1999).
Deghenghi,Romano, "The Development of 'Impervious Peptides' as Growth Hormone Secretagogues," Acta. Paediatr. Suppl. 423(7):85-87 (1997).
Deghenghi, Romano, "Growth Hormone Releasing Peptides," in Growth Hormone Secretagogues pp. 85-102 (Barry B. Bercu and Richard F. Walker eds., Springer-Verlay New York, Inc. 1996).
Deghenghi et al., "Small Peptides as Potent Releasers of Growth Hormone," J. Ped. Endocrinol. Metabol. 8:311-313 (1995).
Furuta et al., "General Pharmacology of KP-102 (GHRP-2), a Protein Growth Hormone-Releasing Peptide," Arznelm-Forsch./Drug Res. 54(12):868-880 (2004).
Ghigo et al., "Growth Hormone-Releasing Peptides," Euro. J. Endocrinol. 136:445-460 (1997).
Ghigo et al., "Reliability of Provocative Tests to Assess Growth Hormone Secretory Status. Study in 472 Normally Growing Children," J. Clinical Endocrinol. Metabol. 81(9):3323-3327 (1996).
Growth Hormone Research Society, "Consensus Guidelines for the Diagnosis and Treatment of Adults with Growth Hormone Deficiency: Summary Statement of the Growth Hormone Research Society Workshop on Adult Growth Hormone Deficiency," J. Clin. Endocrinol. Metabol. 83(2):379-381 (1998).
Growth Hormone Research Society, "Consensus Guidelines for the Diagnosis and Treatment of Growth Hormone (GH) Deficiency in Childhood and Adolescence: Summary Statement of the GH Research Society," J. Clin. Endocrinol. Metab. 85(11):3990-3993 (2000).

(Continued)

Primary Examiner — Elly-Gerald Stoica
(74) Attorney, Agent, or Firm — LeClairRyan, a Professional Corporation

(57) ABSTRACT

A method of assessing growth hormone deficiency in a human or animal subject, the method comprising administering orally to the subject EP 1572 (Formula I) or EP 1573 (Formula II), obtaining a post-administration sample from the subject, determining the level of growth hormone in the sample and assessing whether the level of growth hormone in the sample is indicative of growth hormone deficiency in the subject. Preferably, the GH level in the sample is measured by immunoassay. Also disclosed is a kit of parts constituting a diagnostic kit comprising: (a) EP 1572 or EP 1573 formulated for oral administration; and (b) means for determining the level of growth hormone in a sample.

25 Claims, 2 Drawing Sheets

OTHER PUBLICATIONS

Jansson et al., "Growth Hormone (GH) Assays: Influence of Standard Preparations, GH Isoforms, Assay Characteristics, and GH-Binding Protein," Clin. Chem. 43(6):950-956 (1997).

Juul et al., "European Audit of Current Practice in Diagnosis and Treatment of Childhood Growth Hormone Deficiency," Horm. Res. 58:233-241 (2002).

MacLean et al., "Results of a Phase I Study Investigating the Bioavailability of a Novel Oral Growth Hormone Secretagogue, ARD-07, With and Without Food," Poster Presented at ENDO Jun. 17, 2008.

Mahajan et al., "A Simple Test for Growth Hormone Deficiency in Adults," J. Clin. Endocrinol. Metabol. 85 (4):1473-1476 (2000).

Muccioli et al., "Specific Receptors for Synthetic GH Secretagogues in the Human Brain and Pituitary Gland," J. Endocrinol. 157:99-106 (1998).

Muccioli et al., "Tissue Distribution of GHRP Receptors in Humans," IV European Congress of Endocrinology, Oral Session:OR15-7 Sevilla, Spain (May 9-13, 1998).

Piccoli et al., "Pharmacokinetics and Pharmacodynamic Effects of an Oral Ghrelin Agonist in Healthy Subjects," J. Clin. Endocrinol. Metabol. 92(5):1814-1820 (2007).

Pihoker et al., "Diagnostic Studies with Intravenous and Intranasal Growth Hormone-Releasing Peptide-2 in Children of Short Stature," J. Clin. Endocrinol. Metabol. 80(10):2987-2992 (1995).

Ranke, Michael B., "Diagnosis of Growth Hormone Deficiency and Growth Hormone Stimulation Tests," in Diagnostics of Endocrine Function in Children and Adolescents pp. 107-128 (Michael B. Rarke ed. Basel, Kager 2003).

Smith, Roy G., "Development of Growth Hormone Secretagogues," Endocrine Reviews 26(3):346-360 (2005).

Strasburger, Christian J., "Methods in Determining Growth Hormone Concentrations: An Immunofunctional Assay," Pediatrics 104:1024-1028 (1999).

Styne, Dennis M., "Growth," in Basic & Clinical Endocrinology pp. 128-159 (Francis S. Greenspan and John D. Baxter eds., 4th ed., Appletone & Lange 1994).

Veeraragavan et al, "Growth Hormone-Releasing Peptide (GHRP) Binding to Porcine Anterior Pituitary and Hypothalamic Membranes," Life Sciences 50:1149-1155 (1992).

Yuen, Kevin, "The New, Oral GH Secretagogue (ARD-07) as a GH Stimulation Test may be an Alternative to the Insulin Tolerance Test in the Diagnosis of GH Deficiency in Adults with Primary Hypothalamic Disease," 2008 Endocrine Society's 90th Annual Meeting.

Bowers et al., "The Growth Hormone-releasing Activity of a Synthetic Hexapeptide in Normal Men and Short Statured Children After Oral Administration," Journal of Clinical Endocrinology and Metabolism 74:292-298 (1992).

Mealy et al. "EP-1572 (JMV-1843)," Drugs of the Future 29:1140 (2004).

Galloway et al., "Safety of the Insulin Tolerance Test," Arch. Dis. Child 87:354-356 (2002).

Document No. PILIC0082E, "Insulin Tolerance Test," Coordinating Committee in Paediatrics, 2007.

Bellone et al., "Growth Hormone-Releasing Effect of Oral Growth Hormone-Releasing Peptide 6 (GHRP-6) Administation in Children with Short Stature," Eur. J. Endocrinol. 133:425-429 (1995) (abstract).

Petersenn et al., "Diagnosis of Growth Hormone Deficiency in Adults by Testing with GHRP-6 Alone or in Combination with GHRH: Comparison with the Insulin Tolerance Test," Eur. J. Endocrinol. 146:667-672 (2002) (abstract).

METHODS AND KITS TO DIAGNOSE GROWTH HORMONE DEFICIENCY BY ORAL ADMINISTRATION OF EP 1572 OR EP 1573 COMPOUNDS

This application is a U.S. national stage entry under 35 U.S.C. §371 of International Patent Application No. PCT/GB2007/000566, filed Feb. 19, 2007, which claims priority from Great Britain Patent Application No. 0603295.7, filed Feb. 18, 2006.

The present invention relates to methods and kits for use in relation to the diagnosis of growth hormone deficiency in a human or animal subject.

An estimated 1 out of 4000 school children is affected by growth hormone deficiency (GHD), with idiopathic hypopituitarisms being the most common cause.

It is recognised in children with GHD that short stature may be the only feature present. The Growth Hormone Research Society suggest that if certain criteria are present, then an immediate investigation should be initiated, these include: 1) severe short stature, defined as a height more than 3 standard deviations (SD) below the mean; 2) height more than 1.5 SD below the mid-parental height; 3) height more than 2 SD below the mean and a height velocity over 1 year more than 1 SD below the mean for chronological age, or a decrease in height SD of more than 0.5 over 1 year in children over 2 years of age; 4) in the absence of short stature, a height velocity more than 2 SD below the mean over 1 year or more than 1.5 SD sustained over 2 years; 5) signs indicative of an intracranial lesion; 6) signs of multiple pituitary hormone disorders (MPHD); and 7) neonatal symptoms and signs of GHD (Growth Hormone Research Society, *J. Clin. Endocrinol. Metab.* (2000), 85(11), p 3990-3993).

However, GHD is no longer considered to be simply a pediatric condition associated with poor growth velocity. Adults still need adequate levels of GH to maintain a healthy body composition and metabolism. Adults with GHD have increased abdominal fat, impaired cardiac function, elevated cholesterol levels, and reduced exercise capacity, lean body mass and bone mineral content (Growth-Hormone Research Society, *J. Clin. Endocrinol. Metab.* (1998), 83(2), p 379-381). A test that provokes the pituitary to release GH is used to diagnose GHD in both adults and children. There are a variety of agents which provoke the release of growth hormone, including levodopa, clonidine, arginine, insulin, growth hormone releasing hormone (GHRH) and various analogues of GHRH have been used, either singly or in combination, to assess GH secretory capability in children with short stature and adults with a range of conditions associated with GHD, (see Greenspan, F. and Baxter, J. D., Chapter 3, *Basic & Clinical Endocrinology*, 4$^{th}$ Ed. (1994) Prentice Hall, USA; WO 94/11396; and WO 94/11397).

Apart from insulin and the combination of GHRH plus arginine, the above agents either suffer from a low sensitivity ("sensitivity" being the proportion of subjects who are correctly diagnosed with GHD) or a low specificity ("specificity" being the proportion of subjects who are correctly assessed as not having GHD), this is mainly due to considerable variability in GH response between subjects and also a high rate of false positive results. A summary of the sensitivities and specificities is included in Table 1 below; ideally, a provocative agent should have both a sensitivity and specificity ≧95% (see Biller, B. M. K. et al. *J. Clin. Endocrinol. Metab.* (2002), 87(5), p 2067-2079).

| Test | Sensitivity | Specificity |
| --- | --- | --- |
| ITT (i.v.) | 96% | 92% |
| ARG-GHRH (i.v.) | 95% | 91% |
| ARG-L-DOPA (p.o) | 97% | 79% |
| ARG (i.v.) | 87% | 91% |
| L-Dopa (p.o.) | 100% | 62% |

The intravenous insulin intolerance test (ITT) is considered to be the best screening method for GHD diagnosis (Mahajan et al. *J. Clin. Endocrin. & Metab.* (2000), p 1473-1476). However, this test carries the risk of causing the subject serious harm (for example by causing a diabetic coma due to hypoglycaemia) and therefore the subject must be continuously observed for a prolonged period of time in an appropriately staffed investigation unit. This makes the ITT very expensive as a screening procedure outside very specialised centres.

The GHRH plus L-arginine test is now considered to be almost as predictive as the ITT test. However, it can provoke a range of side effects including vasodilation or flushing, paresthesias, nausea and abnormal taste sensation (Biller, B. M. K. et al. *J. Clin. Endocrinol. Metab.* (2002), 87(5), p 2067-2079).

In all of the above tests, multiple samples must often be taken over a period of hours in order to establish a diagnosis. Additionally, the other tests mentioned above produce side effects that include nausea, vomiting, paresthesias, dizziness, astbenia and headaches (ibid).

In the last few years, several investigators have demonstrated that GH secretion can be stimulated by synthetic oligopeptides termed GH-releasing peptides (GHRP) such as hexarelin and various hexarelin analogs (Ghigo et al., *European Journal of Endocrinology*, 136, 445-460, 1997). These compounds act through a mechanism which is distinct from that of GHRH (C. Y. Bowers, in "Xenobiotic Growth Hormone Secretagogues", Eds. B. Bercu and R. F. Walker, Pg. 9-28, Springer-Verlag, New York 1996) and by interaction with specific receptors localized in the hypothalamus and pituitary gland ((a) G. Muccioli et al., *Journal of Endocrinology*, 157, 99-106, 1998; (b) G. Muccioli, "Tissue Distribution of GHRP Receptors in Humans", Abstracts IV European Congress of Endocrinology, Sevilla, Spain, 1998). Recently it was demonstrated that GHRP receptors are present not only in the hypothalamo-pituitary system but also in various human tissues not generally associated with GH release (G. Muccioli et al., see above (a)).

GHRPs and their antagonists are described, for example, in the following publications: C. Y. Bowers, supra, R. Deghenghi, "Growth Hormone Releasing Peptides", ibid, 1996, pg. 85-102; R. Deghenghi et al., "Small Peptides as Potent Releasers of Growth Hormone", *J. Ped. End. Metab.*, 8, pg. 311-313, 1996; R. Deghenghi, "The Development of Impervious Peptides as Growth Hormone Secretagogues", *Acta Paediatr. Suppl.*, 423, pg. 85-87, 1997; K. Veeraraganavan et al., "Growth Hormone Releasing Peptides (GHRP) Binding to Porcine Anterior Pituitary and Hypothalamic Membranes", *Life Sci.*, 50, Pg. 1149-1155, 1992; and T. C. Somers et al., "Low Molecular Weight Peptidomimetic Growth Hormone Secretagogues", WO 96/15148 (May 23, 1996), WO 95/14666, WO 01/96300, WO 91/18016, WO 96/10040, WO 97/22620, WO 99/62539, U.S. Pat. No. 5,646,301, U.S. Pat. No. 5,955,421, U.S. Pat. No. 5,872,100, U.S. Pat. No. 5,668,254, U.S. Pat. No. 5,635,379, U.S. Pat. No. 6,025,471.

Growth hormone releasing peptide 6 (GHRP-6) has been used as a provocative agent for the diagnosis of GHD in conjunction with GHRH (U.S. Pat. No. 5,811,074). This method relies upon the intravenous administration of GHRP-6 and GHRH and involves a prolonged test period with multiple samples necessary to arrive at a diagnosis.

Growth hormone releasing peptide 2 (GHRP-2) has been shown to have some utility in the diagnosis of GHD when administered to a subject via intravenous injection or intranasal administration (Pihoker et al. *J. Clin. Endocrin. & Metab.* (1995), p 2987-2992). It was also noted that when GHRP-2 was combined with GHRH, via intravenous administration, a synergistic effect occurred, producing more accurate results. However, the methodology described requires a period of hours and multiple samples from the subject before a diagnosis can be made.

In a refinement of the above test (Mahajan et al. *J. Clin. Endorin. & Metab.* (2000), p 1473-1476), GHRP-2 and GHRH are administered together intravenously and a single sample of blood is taken to provide the diagnosis. No suggestion is made in the document that oral administration would be effective for this combination treatment.

The pharmaceutical company Kaken has recently released a diagnostic kit for GHD onto the Japanese market, using GHRP-2, which is approved for administration intravenously.

The inventors have now found that the oral administration of growth hormone secretagogues (GHSs) EP 1572 and EP 1573 can be used effectively and reliably to diagnose GHD.

EP 1572 (Formula I) or EP 1573 (Formula II) are GHSs (see WO 01/96300, Example 1 and Example 58 which are EP 1572 and EP 1573, respectively) that may be given orally.

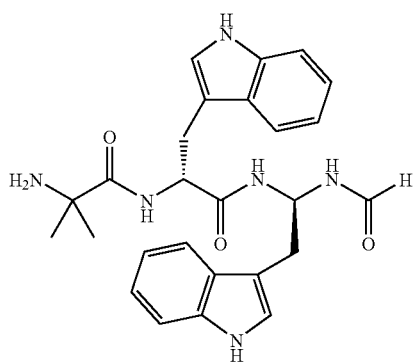

Formula I

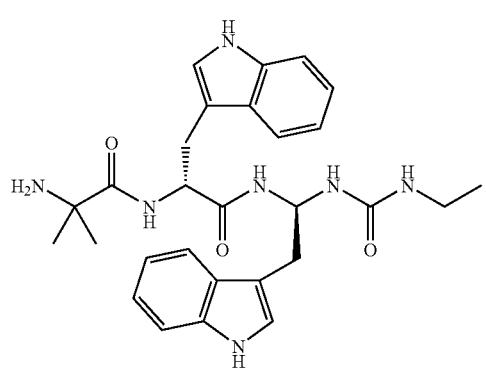

Formula II

EP 1572 and EP 1573 can also be defined as H-Aib-D-Trp-D-gTrp-CHO and H-Aib-D-Trp-D-gTrp-C(O)NHCH$_2$CH$_3$. Wherein, His hydrogen, Aib is aminoisobutyl, D is the dextro isomer, Trp is tryptophan and gTrp is a group of Formula III:

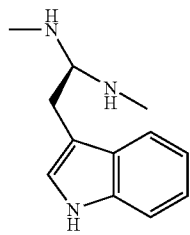

Formula III

A first aspect of the invention provides a method of assessing growth hormone deficiency (GHD) in a human or animal subject, the method comprising administering orally to the subject EP 1572 or EP 1573, obtaining at least one post-administration sample from the subject, determining the level of growth hormone (GH) in the sample or samples and assessing whether the level of GH in the sample or samples is indicative of GHD in the subject.

Typically, the level of GH in the at least one post-administration sample is compared with the level that may be found in an equivalent post-administration sample from a subject who is known not to have GHD and/or the level that may be found in an equivalent post-administration sample from a subject who is known to have GHD. Conveniently, the peak concentration of GH released in the subject to be treated following administration of EP 1572 or EP 1573 may be compared to the peak concentration that may be found in a subject who is known not to have GHD and/or the peak concentration that may be found in a subject known to have GHD, in both cases following administration of EP 1572 or EP 1573.

Preferably, the amount of EP 1572 or EP 1573 administered to a subject is between 18 and 75 mg. Typically the amount administered is 0.5 mg/kg, but may be from 0.1 mg/kg to 1.0 mg/kg or an amount specified by the physician. It may be necessary to use a higher dose in subjects who are obese. It will be appreciated that, typically, the amount of EP 1572 or EP 1573 given to the subject is an amount which provokes the maximal release of GH possible in that subject. Typically, the amount given to the subject is between one and three times the minimum amount which provokes the maximal release of GH in the subject.

In any event, the physician, or the skilled person, will be able to determine the actual dosage that will be most suitable for an individual subject, which may vary with the species, age, weight, sex, renal function, hepatic function and response of the particular subject to be treated with EP 1572 or EP 1573. The above-mentioned dosages are exemplary of the average case; there can, of course, be individual instances where higher or lower dosage ranges are merited, and such are within the scope of this invention.

Preferably, at least one pre-administration sample is taken before the administration of EP 1572 or EP 1573 and one or more post-administration samples are taken at suitable time intervals after administration. The time interval between each sample can be between 15 and 30 minutes and samples may be taken up to 3 hours post administration. More preferably, samples are taken at −30 and/or −15, 0, 15, 30, 60, 90 and 120 minutes relative to the time of oral administration of EP 1572 or EP 1573. Typically, one or two samples are taken prior to administration of EP 1572 or EP 1573, and typically two or three or four or five samples are taken at varying times after administration of EP 1572 or EP 1573.

It will be appreciated that the invention includes a method of diagnosing whether a human or animal subject is suffering from GHD, the method comprising orally administering EP 1572 or EP 1573 to the subject and obtaining a sample from the human or animal subject, determining the level of GH in the sample and assessing whether the level is indicative of GHD in the subject. It will be appreciated that this assessment may aid diagnosis, and may be used in association with other tests, or observations by the physician, in reaching a diagnosis.

The invention includes the oral administration of EP 1572 or EP 1573 to a subject, obtaining a post-administration sample from the subject, determining the level of growth hormone (GH) in the sample and assessing whether the level of GH in the sample is indicative of GHD in the subject.

A second aspect of the invention provides a method of assessing GHD in a human or animal subject, the method comprising providing at least one post-administration sample from a subject who has been orally administered EP 1572 or EP 1573, determining the level of growth hormone (GH) in the sample or samples and assessing whether the level of GH in the sample or samples is indicative of growth hormone deficiency in the subject.

The human or animal subject in either aspect may be a child or an adult. The animal subject may be any mammalian subject but typically is selected from the group consisting of horses, cows, pigs, sheep, goats, cats and dogs.

Preferably, a sample is provided from the subject which was taken before the administration of EP 1572 or EP 1573 (ie pre-administration sample) and one or more samples are provided which were taken from the subject after a suitable time interval after administration (ie post-administration sample). The time interval between each sample can be between 15 and 30 minutes. More preferably, samples provided were taken from the subject at −30 and/or −15, 0, 15, 30, 60, 90 and 120 minutes relative to the time of oral administration of EP 1572 or EP 1573. Typically, one or two samples provided were taken prior to administration of EP 1572 or EP 1573, and typically two or three or four or five samples provided were taken at varying times after administration of EP 1572 or EP 1573.

It will be appreciated that the invention includes a method of diagnosing whether a subject is suffering from GHD, the method comprising providing at least one post-administration sample from a subject who has been orally administered EP 1572 or EP 1573, determining the level of growth hormone (GH) in the sample or samples and assessing whether the level of GH in the sample or samples is indicative of growth hormone deficiency in the subject.

The invention includes the oral administration of EP 1572 or EP 1573 to a subject, providing a post-administration sample from the subject, determining the level of growth hormone (GH) in the sample and assessing whether the level of GH in the sample is indicative of GHD in the subject.

Typically, the level of GH in the at least one post-administration sample is compared with the level that may be found in an equivalent post-administration sample from a subject who is known not to have GHD and/or the level that may be found in an equivalent post-administration sample from a subject who is known to have GHD. Conveniently, the peak concentration of GH released in the subject to be treated following administration of EP 1572 or EP 1573 may be compared to the peak concentration that may be found in a subject who is known not to have GHD and/or the peak concentration that may be found in a subject known to have GHD, in both cases following administration of EP 1572 or EP 1573.

It will be recognised that the invention can be used for the diagnostic assessment of children who have short stature or of children who could be suspected to have GHD, for example, a child who has survived cancer (e.g. leukaemia), undergone brain surgery and/or pituitary surgery and/or chemotherapy and/or radiotherapy and/or brain injury.

It will also be recognised that the invention can be used for the diagnostic assessment of adults who were diagnosed with GHD in childhood, or in adults who could be suspected to have GHD, for example, an adult who has survived cancer, undergone brain surgery and/or pituitary surgery and/or chemotherapy and/or radiotherapy and/or brain injury and/or an adult who has, or who has had treatment for, a pituitary adenoma.

Furthermore, it will also be recognised that certain subject populations who would normally be tested for GHD may benefit from this diagnostic assessment, for example subjects with HIV.

Preferably, the subject will have been on an overnight fast before the administration of EP 1572 or EP 1573. Additionally, if it is known that the subject suffers from other hormonal disorder(s), they may be on a suitable treatment regimen to stabilise that disorder before being subjected to GHD diagnosis (eg treatment of hypothyroidism with levothyroxine).

Pre-administration sample means a sample which is taken from the subject before the oral administration of EP 1572 or EP 1573.

Post-administration sample means a sample which is taken from the subject after the oral administration of EP 1572 or EP 1573.

The sample from the human or animal subject may be any suitable sample. In particular embodiments of the invention, a suitable sample is obtained from the human or animal subject who is to be assessed (eg diagnosed), and this sample is provided for analysis of the level of GH. Conveniently, the sample is a fluid sample and it may be blood, serum or plasma. It is particularly convenient if the sample is a blood sample taken from or provided by the subject wherein the level of growth hormone in the sample is measured using any suitable means for determining the level of GH in a sample.

Examples of suitable means for determining the level of OH in a sample are, but are not limited to, those which make use of agents which selectively bind GH, such as antibodies or antibody like molecules, to determine GH (eg immunoassays). These include a polyclonal antibody-based immunoradiometric assay (p-IRMA), a monoclonal antibody based IRMA (m-IRMA), a monoclonal antibody-based time-resolved immunofluorometric assay (trIFMA), a radio receptor assay, a bioassay and an immunofunctional assay (IFA) (see Ranke, M. B. (ed): *Diagnostics of Endocrine Function in Children and adolescents*, Basel, Karger, 2003, pp 107-128 and Chatarine Jansson, et al., *Clin. Chem.* (1997) 43(6), pp 950-956). Examples of the above assays include: Microwell ELISA human growth hormone immunoassay test kit from Diagnostic Automation INC., Calabasas, Calif. 91302 USA (catalogue number 1901); Immunoassay for the quantitative determination of human GH from Nichols Diagnostic Institute, San Juan Capistrano, Calif., US (catalogue number 62-7056); and human GH IRMA kit, Institute of Isotopes Co. Ltd., Budapest, Hungary.

The level of GH in the post-administration sample or samples and/or the kinetics of GH production as determined by measuring the level of GH in the post-administration samples may be used to assess whether the human or animal subject has GHD. GH levels, or GH production kinetics, which are indicative of GH deficiency are readily determined and parameters are used which give good specificity and sensitivity. As discussed above, the measured levels can be compared to levels that may be found in known GHD subjects or normal subjects (no GHD) who have been subjected to the same test regime. In one embodiment of the invention a cut-off level of GH found following maximal provocations using EP 1572 or EP 1573 may be used to assess GHD. Suitable cut-off levels for particular doses of EP 1572 and EP 1573 are readily determined.

A third aspect of the invention provides for the use of EP 1572 or EP 1573 in a kit for assessing growth hormone deficiency in a human or animal subject. Typically, the kit is used for diagnosing GHD in a human or animal subject.

The invention includes the use of EP 1572 or EP 1573 in a kit for assessing growth hormone deficiency in a human or animal subject, wherein EP 1572 or EP 1573 are administered orally. Typically, the kit is used for diagnosing GHD in a human or animal subject.

A fourth aspect of the invention provides the use of EP 1572 or EP 1573 in the manufacture of a composition for oral administration for assessing growth hormone deficiency in a human or animal subject.

Preferably, the composition contains a suitable amount of EP 1572 or EP 1573 in a single oral dose. Typically, the assessment of GHD in the human or animal subject is done by measuring the levels of GH in sample(s) taken after administration of EP 1572 or EP 1573 (post-administration sample(s)). Typically, at least one sample is taken before administration of EP 1572 or EP 1573 (pre-administration sample).

The invention includes the use of EP 1572 or EP 1573 in the manufacture of a composition for oral administration for assessing growth hormone deficiency in a human or animal subject.

A fifth aspect of the invention provides a kit of parts constituting a diagnostic kit comprising:
(a) EP 1572 or EP 1573 formulated for oral administration; and
(b) means for determining the level of growth hormone in a sample.

Preferably, the composition contains a suitable amount of EP 1572 or EP 1573 in a single oral dose. Typically, the assessment of GHD in the human or animal subject is done by measuring the levels of GH in sample(s) taken after administration of EP 1572 or EP 1573 (post-administration sample). Typically, a sample is taken before administration of EP 1572 or EP 1573 (re-administration sample) and the peak level of GH in the post-administration sample is determined. Preferably, the means for determining the level of GH is as defined above. More preferably the means for determining the level of GH in a sample are, but are not limited to, those which make use of agents which selectively bind GH, such as antibodies or antibody like molecules to determine GH (eg immuno assays) such as a polyclonal antibody-based immunoradiometric assay (p-IRMA), a monoclonal antibody based IRMA (m-IRMA), a monoclonal antibody-based time-resolved immunofluorometric assay (trIFMA), a radio receptor assay, a bioassay or an immunofunctional assay (IFA).

The kit of parts may further comprise a set of instructions on the use of the diagnostic kit, setting out the steps needed to arrive at a diagnosis. Preferably the means for determining the level of growth hormone in a sample is an immunoassay.

The kit of parts may also be considered to be a system for the assessment of GHD. Typically, the system contains EP 1572 or EP 1573 in an oral formulation and an immunoassay for GH.

Additionally, although EP 1572 or EP 1573 are useful on their own for assessing GHD in a human or animal subject, there may be a benefit of using EP 1572 or EP 1573 in combination with one or more provocative agents, such as levodopa, clonidine, arginine, insulin, growth hormone releasing hormone (GHRH), various analogues of GHRH, GHRP(s) for assessing GHD in a human or animal subject. Alternatively, EP 1572 or EP 1573 may be used in combination with or as an adjuvant to another test for GHD, such as the tests defined in the guidelines of the Growth Hormone Society (*J. Clin. Endocrinol. Metab.* (2000), 85(11), p 3990-3993) and *J. Clin. Endocrinol. Metab.* (1998), 83(2), p 379-381).

Thus, in the methods of the first and second aspect of the invention, the human or animal subject may be administered one or more other provocative agents as well as EP 1572 or EP 1573. Similarly, in the third and fifth aspects of the invention the kit may also contain one or more other provocative agents as well as EP 1572 or EP 1573. In the fourth aspect of the invention the composition may additionally comprise one or more other provocative agents, or the human or animal subject may be administered one or more provocative agents.

It will be appreciated that the human or animal subject may have separately and independently been assessed for GHD using one or more other provocative agents.

The methods and kits of the invention may also have the advantage that they may be more efficacious than, be less toxic than, produce fewer side effects than, and/or have a better pharmacokinetic profile than, and/or have other useful pharmacological properties than methods and kits known in the prior art, whether for use in the above-stated indications or otherwise.

The listing or discussion of a prior-published document in this specification should not necessarily be taken as an acknowledgement that the document is part of the state of the art or is common general knowledge.

All documents cited in the patent specification are hereby incorporated herein by reference.

The invention will now be described in more detail by reference to the following non-limiting Examples and Figures wherein.

EXAMPLE 1

Figure 1:
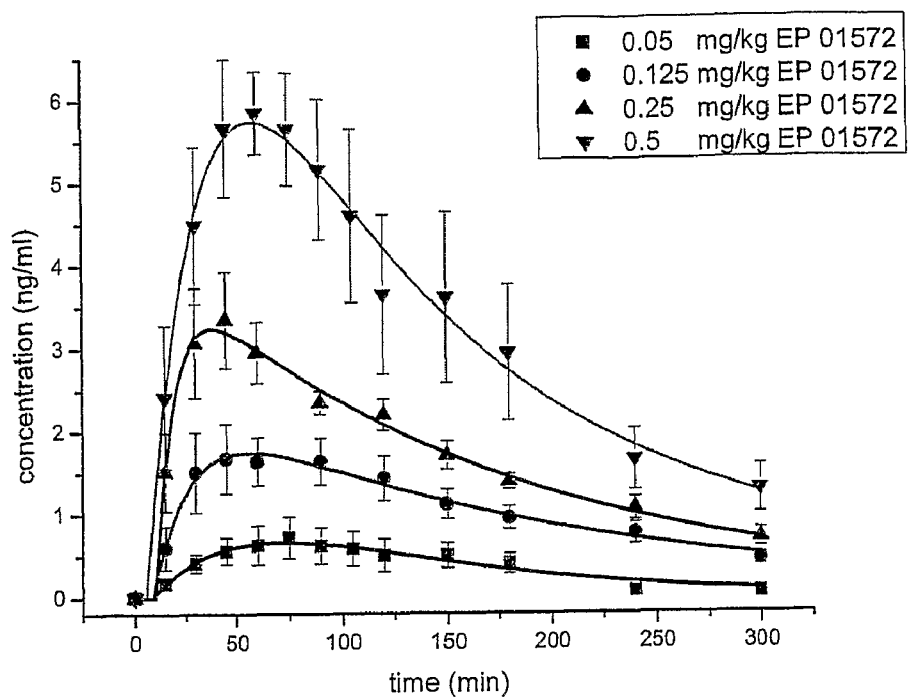
FIG. 1 shows plasma concentrations of EP 1572 (means±SEM) after oral administration of different doses of EP 1572 in healthy male subjects.

Oral Bioavailability of EP 1572 and Induction of GH Following Oral Administration After a provocative test with EP 1572, the pharmacokinetic profile of EP 1572 and the level of GH released in response to its oral administration were established in 36 healthy male subjects at various doses.

The formulations for each dose used for a subject weighing 70 kg are described below:

For 0.005 mg/kg, 6 mg of EP 1572 was dissolved in 40 mL of distilled water. A 2.33 mL aliquot of this solution was diluted by 17.67 mL of water to generate the final dose formulation as a 20 mL solution.

For 0.05 mg/kg, 15 mg of EP 1572 was dissolved in 40 mL of distilled water. A 9.33 mL aliquot of this solution was diluted by 10.67 mL of water to generate the final dose formulation as a 20 mL solution.

For 0.125 mg/kg, 8.75 mg of EP 1572 was dissolved in a solution containing 20 mL of distilled water and 40 μL of a 1 molar solution of hydrochloric acid.

For 0.25 mg/kg, 17.5 mg of EP 1572 was dissolved in a solution containing 20 mL of distilled water and 40 μL of a 1 molar solution of hydrochloric acid.

For 0.5 mg/kg, 35 mg of EP 1572 was dissolved in a solution containing 20 mL of distilled water and 40 μL of a 1 molar solution of hydrochloric acid.

From the subject a blood sample was drawn at 30 and 15 minutes before the administration of EP 1572. A sample of blood was taken from the subject immediately before the aqueous formulation containing 0.5 mg/kg of EP 1572 was orally administered to the subject. Further blood samples were taken from the subject at 15, 30, 60, 90, 120, 150, 180, 210, 240, 270 and 300 minutes from administration and a portion of each sample processed according to the assay protocol outlined below. The level of GH present in each sample was determined by the assay method outlined below and the peak concentration ($C_{max}$) for the subject determined. The remainder of the sample was used to determine the level of EP 1572 present in the systemic circulation (as outlined below).

GH Level Assay

The assays were performed using the Nichols Advantage® human growth hormone immunoassay using the Nichols Advantage® Specialty System for the qualitative determination of human growth hormone concentrations in human serum, using the materials and methods set out in the standard operating procedures of the manufacturer (Nichols Institute Diagnostics, 1311 Calle Batido, San Clemente, Calif. 92673, USA).

Assay to Determine Levels of EP 1572 in Blood

The organic components in human plasma were extracted using a total of 500 mL of an ethyl acetate/iso-propanol mixture (82.5% and 17.5%, respectively). After drying (using sodium sulfate) and concentration of the collected organic fractions, the analyte was separated by reverse-phase HPLC (Merck, reverse-phase silica gel, LiChroCART, 125×4 mm) using an eluent mixture of methanol, water and formic acid (65%, 35% and 0.1%, respectively) and detected by a mass spectrometer (Finnigan TSQ 7000). Quantification was performed with EP 1573 as an internal standard (peak area ratio evaluation).

Further dosing studies were carried out wherein the subjects were administered doses of 0.005, 0.05, 0.25 and 0.125 mg/kg each, using the formulations described above.

Figure 2:
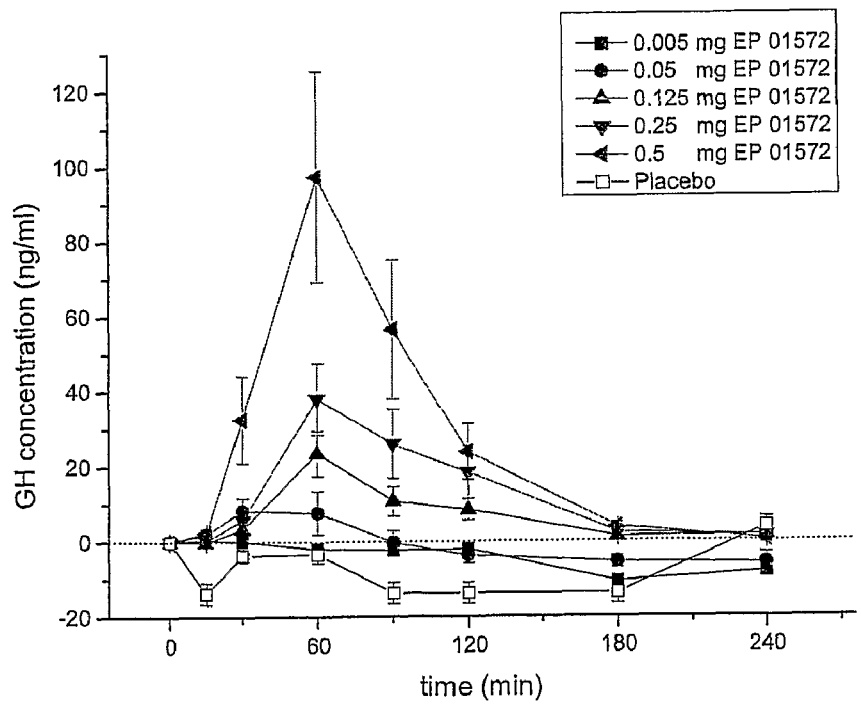
FIG. 2 shows plasma concentrations of growth hormone released after administration of different doses of EP 1572 in healthy male subjects.
Figure 3:
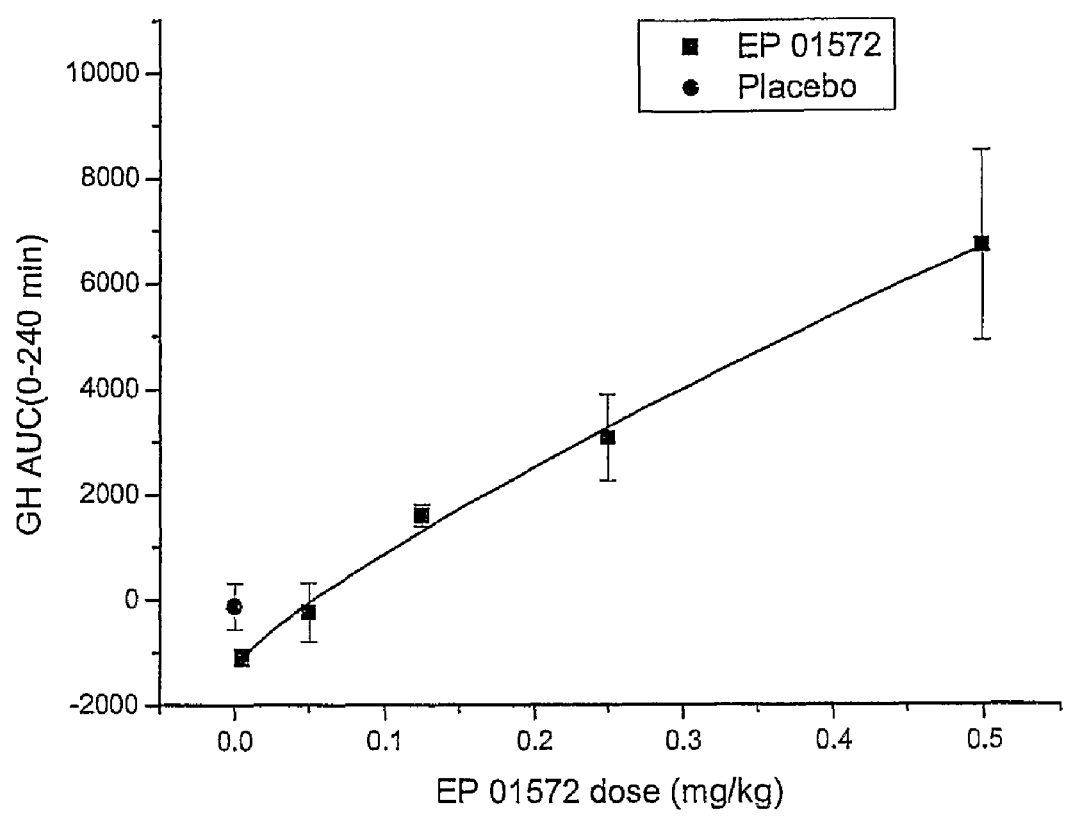
FIG. 3 shows the dose-response of different doses of oral EP 1572 to total GH secretion over the baseline in healthy male subjects.

The results are reported in FIGS. 1 to 3 and Table 2 below.

TABLE 2 pharmacokinetic parameters after oral administration of EP 1572

| Dose (mg/kg) | AUC (0-300) | Cmax (ng/mL) | Tmax (min) |
|---|---|---|---|
| 0.5 | 967.30 ± 149.90 | 7.59 ± 0.83 | 50.00 ± 9.35 |
| 0.25 | 520.03 ± 37.55 | 3.92 ± 0.57 | 55.00 ± 13.78 |
| 0.125 | 320.79 ± 48.63 | 2.33 ± 0.39 | 62.50 ± 14.71 |
| 0.05 | 104.19 ± 33.34 | 0.86 ± 0.24 | 75.00 ± 12.99 |

(mean ± SEM)
AUC = Area under the curve
Cmax = Maximum observed concentration
Tmax = Time to reach maximum observed concentration

EXAMPLE 2

Comparison of the Sensitivity and Specificity of EP 1572 to the GHRH+Arg Test

A subject (either healthy or who has suspected adult-onset hypothalamic-pituitary disease or multiple pituitary hormone deficiencies) is either subjected to the GHRH plus L-arginine test or to a test utilising orally administered EP 1572.

The GHRH plus L-arginine test is carried out as described in Biller, B. M. K. et al. *J. Clin. Endocrinol. Metab.* (2002), 87(5), p 2067-2079, with a dose of 1 μg/kg of GHRH administered by iv bolus, followed by a 30 minute infusion of 30 g of L-arginine. Blood samples are taken from the subject at −30 or −15, 0, 15, 30, 60, 90, 120 and 150 minutes after administration.

The EP 1572 test is carried out as described above using a dose of 0.5 mg/kg and blood samples are taken from the subject at −30 or −15, 0, 15, 30, 60, 90, 120 and 150 minutes after administration.

After at least seven days the subjects who had been subjected to the GHRH plus L-arginine test are subjected to the EP 1572 test and vice versa.

The samples may then be analysed as described in the above-referenced assay and the results used to determine whether a subject has GHD or not based upon the statistical analysis of the results (95% sensitivity and 95% specificity), as described in Biller, B. M. K. et al. *J. Clin. Endocrinol. Metab.* (2002), 87(5), p 2067-2079.

EXAMPLE 3

Standard Protocol

A 50 mg sample of EP 1572 is dissolved, with shaking, in a 250 mL graduated vial by the portion wise addition of 100 mL of purified water. Alternatively, two dispersible tablets each containing 25 mg of EP 1572 can be dissolved in a similar manner.

From the subject a blood sample is drawn at 15 minutes before the administration of EP 1572. A sample of blood is taken from the subject immediately before the aqueous solution of EP 1572 is orally administered to the subject, either at a fixed dose of 50 mg or at a dose of 1 mL per kg of body weight. Further blood samples are taken from the subject at 15, 30, 60, 90 and 120 minutes from administration and the level of GH present in each sample is determined by the assay method described above, the peak level of which is then used to determine whether or not the subject suffers from GHD. The lack of, or a blunted increase in GH concentration would indicate GHD when compared to that of a normal person.

EXAMPLE 4

A Preparation of EP 1572 for Clinical Use

1. Inject with a 50 ml syringe and a needle, 50 ml of water for irrigation into the 100 ml bottle containing EP 1572.
2. Shake vigorously the bottle until a complete dissolution. Open the bottle and pour the solution into a glass beaker/measuring cylinder.
3. Rinse the 100 ml glass bottle with an extra 50 ml water for irrigation and pour the solution into the glass beaker/measuring cylinder to give a final EP 1572 concentration of approximately 0.5 mg/ml.
4. Add the entire contents of the excipient sachet and dissolve it.
5. The appropriate volume of solution is measured out into a separate measuring cylinder according to the subject's weight to give a dose of 0.5 mg/kg EP 1572 (i.e. 1 ml solution per kg body weight).
6. If the subject weighs >100 kg then steps 1-4 are repeated with a second set of ingredients.

7. The solution should be administered to the subject immediately.

EXAMPLE 5

A Preparation of EP 1572 for Clinical Use

The entire contents of a sachet containing EP 1572 (50 mg) and excipients is dissolved (see Table 3 for potential contents of sachet), with shaking, in a vial by the portion wise addition of 100 mL of purified water. The appropriate volume of solution is measured out into a separate measuring cylinder according to the subject's weight to give a dose of 0.5 mg/kg EP 1572 (i.e. 1 ml solution per kg body weight). If the subject weighs >100 kg then a further sachet is dissolved in 100 mL of purified water. The solution should be administered to the subject immediately.

TABLE 3 possible sachet containing 50 mg of EP 1572 and excipients

| Raw Material | Unit Quantity (1 Sachet) | Percentage Quantity |
|---|---|---|
| EP 1572 | 0.0500 g | 5.00% |
| Aerosil 200W (Colloidal silicon dioxide) | 0.0010 g | 0.10% |
| Kollidon CL (Crospovidone) | 0.0200 g | 2.00% |
| Flowlac 100 (Lactose monohydrate) | 0.9190 g | 91.90% |
| Pruv (Sodium Stearyl Fumarate) | 0.0100 g | 1.00% |
| Total | 1.0000 g | 100% |

The invention claimed is:

1. A method of assessing growth hormone deficiency in a human or animal subject, the method comprising:
    administering orally to the subject EP 1572 or EP 1573,
    obtaining at least one post-administration sample from the subject,
    determining the level of growth hormone in the at least one sample and
    comparing the level of growth hormone in the at least one sample to a level of growth hormone in an equivalent post-administration sample from a subject known not to have growth hormone deficiency and/or a level of growth hormone in an equivalent post-administration sample from a subject known to have growth hormone deficiency to assess whether the level of growth hormone in the at least one sample is indicative of growth hormone deficiency in the subject.

2. A method according to claim 1 wherein a pre-administration sample is taken before the administration of EP 1572 or EP 1573.

3. A method according to claim 1 wherein one or more post-administration sample or samples are taken after a suitable time interval.

4. A method according to claim 3 wherein the time interval can be between 15 and 30 minutes between each sample.

5. A method according to claim 1 wherein samples are taken at −30 or −15, 0, 15, 30, 60, 90 and 120 minutes relative to the time of oral administration of EP 1572 or EP 1573.

6. A method according to claim 1 wherein the assessment of the peak level of growth hormone released during the time frame is used to indicate growth hormone deficiency in the subject.

7. A method of assessing growth hormone deficiency in a human or animal subject, the method comprising:
    providing at least one post-administration sample from a subject who has been orally administered EP 1572 or EP 1573,
    determining the level of growth hormone in the at least one sample and
    comparing the level of growth hormone in the at least one sample to a level of growth hormone in an equivalent post-administration sample from a subject known not to have growth hormone deficiency and/or a level of growth hormone in an equivalent post-administration sample from a subject known to have growth hormone deficiency to assess whether the level of growth hormone in the at least one sample is indicative of growth hormone deficiency in the subject.

8. A method according to claim 7 wherein a sample from the subject prior to the administration of EP 1572 or EP 1573 is provided.

9. A method according to claim 7 wherein one or more post-administration sample or samples taken after a suitable time interval are provided.

10. A method according to claim 9 wherein the time interval can be between 15 and 30 minutes.

11. A method according to claim 7 wherein samples taken at −30 or −15, 0, 15, 30, 60, 90 and 120 minutes relative to the time of oral administration of EP 1572 or EP 1573 are provided.

12. A method according to claim 7 wherein the assessment of the peak level of growth hormone released during the time frame is used to indicate growth hormone deficiency in the subject.

13. A method according to claim 7 wherein the human or animal subject may be either a child or an adult.

14. A method according to claim 7 wherein the animal subject is a horse, cow, sheep, pig, goat, cat or dog.

15. The method of claim 7 wherein the amount of EP 1572 or EP 1573 administered to the subject is between 18 and 75 mg.

16. A method according to claim 7 wherein the at least one sample is a blood sample, a serum sample or a plasma sample.

17. A method according to claim 7 wherein the level of growth hormone in the at least one sample is measured using an immunoassay.

18. A kit of parts constituting a diagnostic kit comprising:
    (a) EP 1572 or EP 1573 formulated for oral administration; and
    (b) means for determining the level of growth hormone in a sample.

19. A kit of parts according to claim 18 further comprising a set of instructions on the use of the diagnostic kit, setting out the steps needed to arrive at a diagnosis.

20. A kit of parts according to claim 18 wherein the means for determining the level of growth hormone in a sample is an immunoassay.

21. A method according to claim 1 wherein the human or animal subject may be either a child or an adult.

22. A method according to claim 1 wherein the animal subject is a horse, cow, sheep, pig, goat, cat or dog.

23. The method of claim 1 wherein the amount of EP 1572 or EP 1573 administered to the subject is between 18 and 75 mg.

24. A method according to claim 1 wherein the at least one sample is a blood sample, a serum sample or a plasma sample.

25. A method according to claim 1 wherein the level of growth hormone in the at least one sample is measured using an immunoassay.

* * * * *